United States Patent [19]
Chiu

[11] Patent Number: 5,325,320
[45] Date of Patent: Jun. 28, 1994

[54] AREA EFFICIENT MULTIPLIER FOR USE IN AN INTEGRATED CIRCUIT

[75] Inventor: Chiao-Er A. Chiu, Sunnyvale, Calif.

[73] Assignee: Seiko Epson, Japan

[21] Appl. No.: 877,562

[22] Filed: May 1, 1992

[51] Int. Cl.⁵ ............................................. G06F 7/52
[52] U.S. Cl. ..................................................... 364/760
[58] Field of Search ........................................ 364/760

[56] References Cited

U.S. PATENT DOCUMENTS

| | | | |
|---|---|---|---|
| 4,646,257 | 2/1987 | Essig et al. | 364/760 |
| 4,799,183 | 1/1989 | Nakano et al. | 364/760 |
| 4,972,362 | 11/1990 | Elkind et al. | 364/760 |
| 5,036,482 | 7/1991 | Saini | 364/760 |

OTHER PUBLICATIONS

Cavanagh, *Digital Computer Arithmetic: Design & Implementation* McGraw-Hill Book Co. 1984 pp. 137–233.
Hennessy et al, *Computer Architecture a Quantitative Approach* Morgan Kaufmann Publishers, Inc. 1990 A1–A62.

*Primary Examiner*—David H. Malzahn
*Attorney, Agent, or Firm*—Sterne, Kessler, Goldstein & Fox

[57] ABSTRACT

A high-speed multiplier utilizing a layout architecture requiring very little area on a chip. The present invention employs a floor plan which exemplifies regularity and is approximately 33.3% more compact than conventional Wallace Trees. During a first phase of a first clock cycle, Booth coding takes place resulting in a first group of partial products. In a second phase of the first clock cycle, the first group of partial products are input into a first and a second carry-save adder. Results from the second carry-save adder are latched in a first and second register. Also during the second phase of the first clock cycle, a second group of partial products are Booth coded. In a first phase of a cycle 2, the second group of partial products are input into the first and second carry-save adders. Results from the second carry-save adder are latched into a third and fourth register. In a second phase of cycle 2, results from the first, second, third and fourth registers are input into a third and fourth carry-save adder. The outputs from the fourth carry-save adder are latched into a fifth and a sixth register. In a first phase of a cycle 3, results latched in the fifth and sixth registers are input into a CPA. The CPA then generates a final output for the multiplier.

5 Claims, 5 Drawing Sheets

5 x 3 = 15

```
    0101    MULTIPLICAND
    0011    MULTIPLIER
    ────
    0101  ⎫
   0101   ⎬  SHIFTED
  0000    ⎭  PARTIAL PRODUCTS
 0000
 ───────
 0001111   PRODUCT
```

```
     0101    MULTIPLICAND
     0011    MULTIPLIER
 11111011
  000101     BOOTH'S ALGORITHM
 ────────
 00001111
```

FIGURE 1B (Prior Art)

AREA EFFICIENT MULTIPLIER FOR USE IN AN INTEGRATED CIRCUIT

BACKGROUND OF THE INVENTION

1. Field of the Invention

The present invention relates generally to a multiplier for integrated circuits, very large scale integrated circuits (VLSI), and ultra large scale integrated circuits (ULSI). More particularly, the present invention relates to a high-speed multiplication technique utilizing a layout architecture requiring very little area on a chip.

2. Related Art

Digital systems use a variety of multiplication algorithms. FIG. 1A illustrates a simple example of multiplication where $5 \times 3 = 15$. A binary multiplicand is multiplied by a binary multiplier. A series of shifted partial products are formed of zeros and ones. The shifted partial products are then added, resulting in a product. When an X-bit number is multiplied by a Y-bit number in a digital system, the resulting product will be $X + Y$ bits in length.

In simple binary multiplication, partial products are formed by adding one-bit of the multiplier at a time, starting with the least significant bit of the multiplier. One of the simplest ways to generate partial products is to use AND gates as bit-by-bit multipliers. Using this simple multiplication technique, an X bit multiplier generates X partial products.

Prior approaches employ encoding techniques to reduce the number of partial products. Reducing the number of partial products reduces the number of additions that need to be performed. Reducing the number of additions in turn reduces the number of clock cycles necessary for binary multiplication.

One prior approach employs a Booth algorithm as an encoding technique to reduce the number of partial products by at least one half. The Booth algorithm increases the speed of a multiply operation which is a time-consuming operation. FIG. 1B illustrates Booth coding, which is a powerful algorithm for signed-number multiplication. Booth coding, sometimes called Booth recoding and decoding, essentially reduces the amount of partial products needed to generate a product. An example of Booth's algorithm and implementation in hardware is explained in *Digital Computer Arithmetic: Design and Implementation*, J. F. Cavanagh, chapter 3, McGraw-Hill Book Company (1984)(including Wallace Trees discussed below)(hereby incorporated by reference).

Once partial products are formed, they must be added together. Several types of conventional adders exist. One conventional two input adder is a carry propagate adder (CPA). The CPA adds a sum vector to a carry vector to produce one final sum. A CPA is a type of full adder. A full adder is a circuit that generates the sum of two operand bits plus a carry-in bit. The carry-in bit represents the carry-out of a previous lower-order bit position. The full adder produces two outputs: a sum bit and a carry-out bit.

Another type of adder is a carry-save adder (CSA). The CSA is simply a number of independent full adders or half adders. Full CSAs have three inputs and half CSAs have two inputs. CSAs are useful when multiple additions are performed, which is required in high speed multiplication.

A multiplicity of CSAs save the carry propagation until all the additions are completed. Typically, a CPA is used during a final clock cycle to complete carry propagation for all additions performed by the CSAs.

FIG. 2 illustrates a block diagram of an array multiplier 201. As shown in FIG. 2, two 8-bit numbers can be multiplied together using seven CSAs and a CPA. With the hardware of FIG. 2, multiplication can be pipelined, increasing the total throughput. However, it is typically not possible to fit an array large enough to multiply two double-precision numbers on a single chip and have space left over for other arithmetic operations using the design of FIG. 2.

Thus, VLSI designers tend to use other types of multipliers such as multipass array multipliers and even-/odd multipliers (both not shown). For examples of such designs see *Computer Architecture A Quantitative Approach*, J. Hennessy & D. Patterson, Morgan Kaufmann Publishers, Inc., Appendix A (1990)(including Wallace Trees discussed below)(hereby incorporated by reference). These popular designs, although easier to implement in VLSI, are not the fastest designs available.

One of the fastest designs for increasing the speed of multiplication is a Wallace tree. A conventional Wallace tree multiplier is illustrated in FIG. 3. As shown, the Wallace tree is a combination of CSAs and a CPA. The idea of this design is that two adds proceed in parallel or, to put it another way, most streams of data pass through full adders allowing a multiplicity of pipelined stages. Wallace trees run at a minimum of twice the speed of array multipliers discussed above.

Wallace trees look great on paper. They require fewer gates than other conventional multipliers. Nevertheless, Wallace trees are no longer the choice of VLSI designers, because they are very difficult to implement in VLSI. Designers have discovered that they do not have the simple regular structure needed for VLSI design. Consequently, conventional Wallace trees require a significant amount of area on a chip; leaving less room for other circuitry. Referring to FIG. 3, notice that stages 302, 304, 306 and 308 have no unity. Each stage of the Wallace tree is different from the next. This is part of the reason why Wallace trees are so difficult to implement in silicon. Since Wallace trees have irregular structures they also require a significant amount of effort to verify for correctness. Additionally, mistakes in layout are very difficult to detect due to the Wallace tree's irregular structure. For these reasons VLSI designers have, for the most part, chosen other designs such as binary-tree multipliers (not shown), even though they are not as fast as the Wallace trees.

In short, Wallace trees require an abundance of chip area and require a significant amount of effort to implement due to their irregular structure. Therefore, what is needed is a device as fast as a Wallace tree, but having a regular structure requiring less area on a chip and less effort to implement.

SUMMARY OF THE INVENTION

The present invention is directed to a high-speed technique of multiplication utilizing a layout architecture requiring very little chip area. The present invention employs a highly structured floor plan that exemplifies regularity. The floor plan of the present invention is approximately 33.3% more compact than conventional Wallace Trees.

In addition to having a unique architectural design, the present invention utilizes a unique technique of multiplication by reusing certain elements of the multiplier. For example, the first two CSAs, Booth coding circuit and partial product circuits are reused in subsequent clock cycles. In a first clock phase, a first group of partial products are Booth coded. In a second clock phase, the first group of partial products are input into the first two CSAs, while at the same time, a second group of partial products are Booth coded. In the second phase of the first clock cycle, the first group of partial products are input into a first CSA and a second CSA. Results from the second CSA are latched into a first and a second register. Also, during the second phase of the first clock cycle, a second group of partial products are Booth coded.

In a first phase of a second clock cycle, the second group of partial products are input into the first and second CSAs. Results from the second CSA are latched into third and fourth registers.

In a second phase of the second clock cycle, results from the first, second, third and fourth registers are input into a third CSA and a fourth CSA. The outputs from the forth CSA are latched into fifth and sixth registers.

In a first phase of a third clock cycle, results stored in the fifth and sixth registers are input into a CPA. The CPA then generates a final product for the multiplier.

FEATURES AND ADVANTAGES OF THE INVENTION

One feature of the present invention is to provide a multiplier that requires 33% less real estate (i.e., chip space) than conventional Wallace trees.

Another feature of the present invention is structural regularity.

A further feature of the present invention is to provide a design whereby layout mistakes are readily apparent or more easily recognized and corrected than layout mistakes in conventional Wallace trees.

An additional feature of the present invention is to provide a multiplier with less carry-save adders than conventional Wallace trees.

Further features and advantages of the present invention, as well as the structure and operation of various embodiments of the present invention, are described in detail below with reference to the accompanying drawings.

BRIEF DESCRIPTION OF THE DRAWINGS

FIG. 1A illustrates a simple example of multiplication.

FIG. 1B illustrates an example of Booth algorithm signed-number multiplication.

In the drawings, like reference numbers indicate identical or functionally similar elements. Additionally, the left-most digit of a reference number identifies the drawing in which the reference number first appears.

DETAILED DESCRIPTION OF THE PREFERRED EMBODIMENTS

General Overview

The present invention is directed to a high-speed multiplication technique utilizing a layout architecture requiring very little area on a chip. The present invention includes two embodiments. The first embodiment is directed to an architectural implementation of the present invention. The second embodiment is directed to a method for utilizing the architectural implementation of the present invention. The aforementioned embodiments are discussed in the following sections.

Architecture

One of the key advantages of the present invention over conventional multipliers, and in particular Wallace trees, is in its architecture. The present invention employs a floor plan which exemplifies regularity and is approximately 33.3% more compact than conventional Wallace Trees. The present invention sacrifices very little speed (less than half a machine cycle) in its smaller size.

Figure 4:
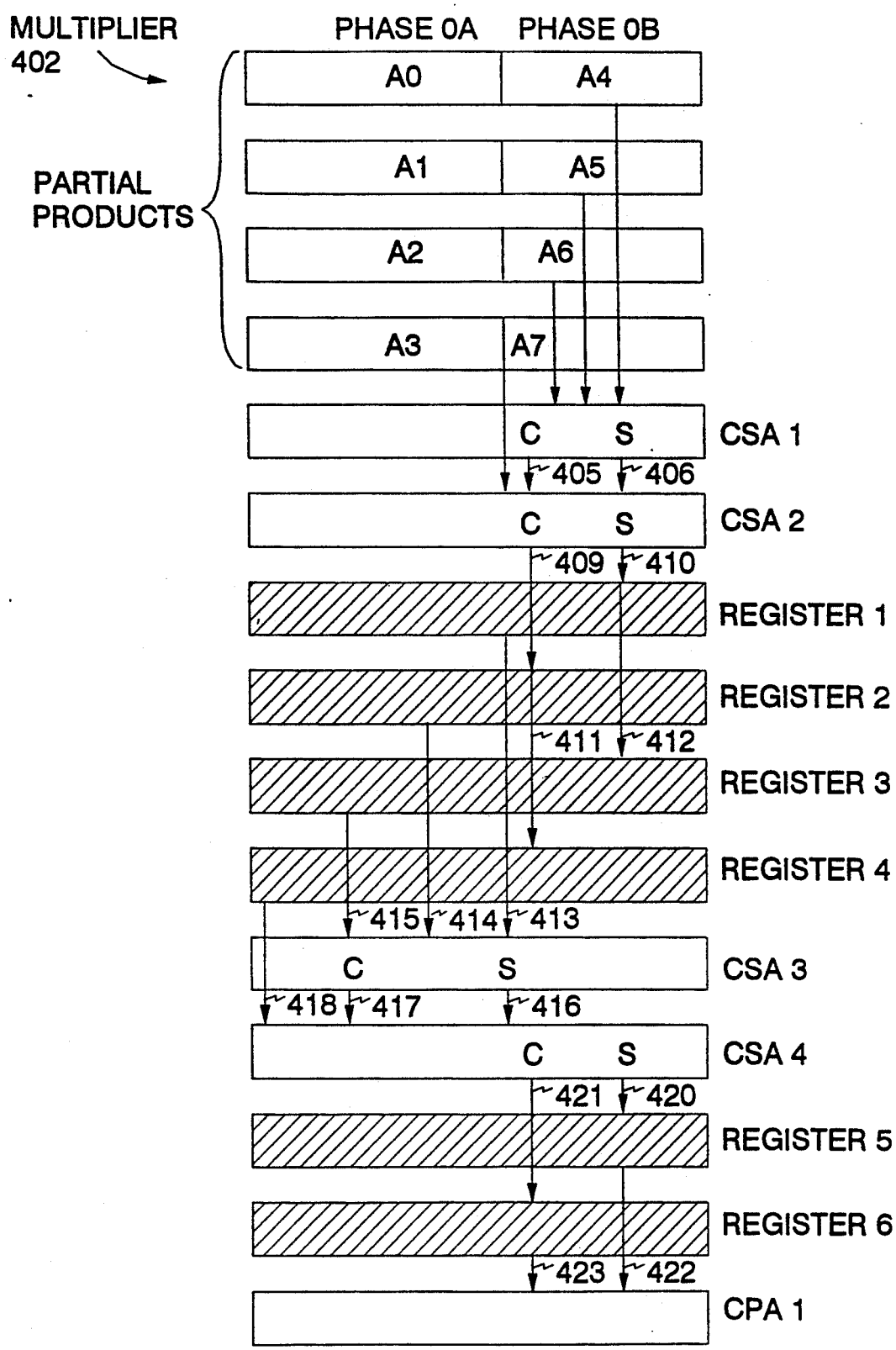
FIG. 4 illustrates a block diagram representing the architecture of a multiplier according to the present invention.

FIG. 4 illustrates a block diagram representing the architecture of a multiplier 402 according to the present invention. Multiplier 402 includes: four carry save adders (CSAs) CSA 1-4, registers 1-4, and a carry propagate adder 1 (CPA 1).

CSAs have three inputs and two outputs. The two outputs of each CSA consist of a sum (S) portion and a carry (C) portion, as shown in FIG. 4. The structure and operation of CSAs are well known to those skilled in the art.

Each register 1-4, has one input and one output. In this example, register 1 has a sum input 410 from CSA2 and an output 413 to CSA3; register 2 has a carry input 409 from CSA2 and an output 414 to CSA3; register 3 has a sum input 412 from CSA2 and an output 415 to CSA3; and register 4 has a carry input 411 from CSA2 and an output 418 to CSA4. Carry inputs 409 and 411 represent different values at different times. Likewise, sum input 410 and sum input 412 represent different values at different times. As will be explained in more detail below, registers 1 and 2 are associated with partial products (A0-A3) and registers 3 and 4 are associated with partial products (A4-A7).

CPA 1 has two inputs 422 and 423. The structure and operation of a CPA are well known to those skilled in the art.

It should be noted that all inputs and outputs from both CSAs and registers are data paths (i.e., sums and carries). Data paths represent buses carrying signal bits of data. The width of the data paths may be any number of bits wide. In the preferred embodiment they are 69 bits wide.

It should also be noted that multiplier 402 employs two less CSAs than conventional Wallace trees. This is primarily accomplished by re-using CSA 1 and CSA 2. As a result, multiplier 402 is more compact than conventional Wallace trees and exemplifies regularity. The regularity of multiplier's 402 design will become more apparent with the discussion below.

Partial products A0-Ax represent incoming data of multiplier 402, wherein x equals any desired number of partial products after Booth coding. A partial product is explained in the background section. Partial products are well known to those skilled in the art. Similarly, Booth coding, hardware structure and operation (explained in the background), are well known to those skilled in the art.

In the example of FIG. 4, there are eight partial products A0-A7. Partial products A0-A7 may be any number of bits wide depending on a particular system's specifications. In the preferred embodiments each partial product Ax is 66 bits wide. The partial products are grouped as follows: A0 with A4, A1 with A5, A2 with A6, and A3 with A7. The first partial product of each group (A0-A3) enter multiplier 402 at a different clock phase than the second partial product of each group (A4-A7) (i.e., PHASE $\phi_1$ and PHASE $\phi_2$). In the preferred embodiment, partial product group A0-A3 enter multiplier 402 during a first clock phase of cycle 1 and partial product group A4-A7 enter multiplier 402 during a second clock phase of cycle 1. However, partial groups are not limited to entering multiplier 402 at these exact phases or clock cycles.

Timing

Figure 2:
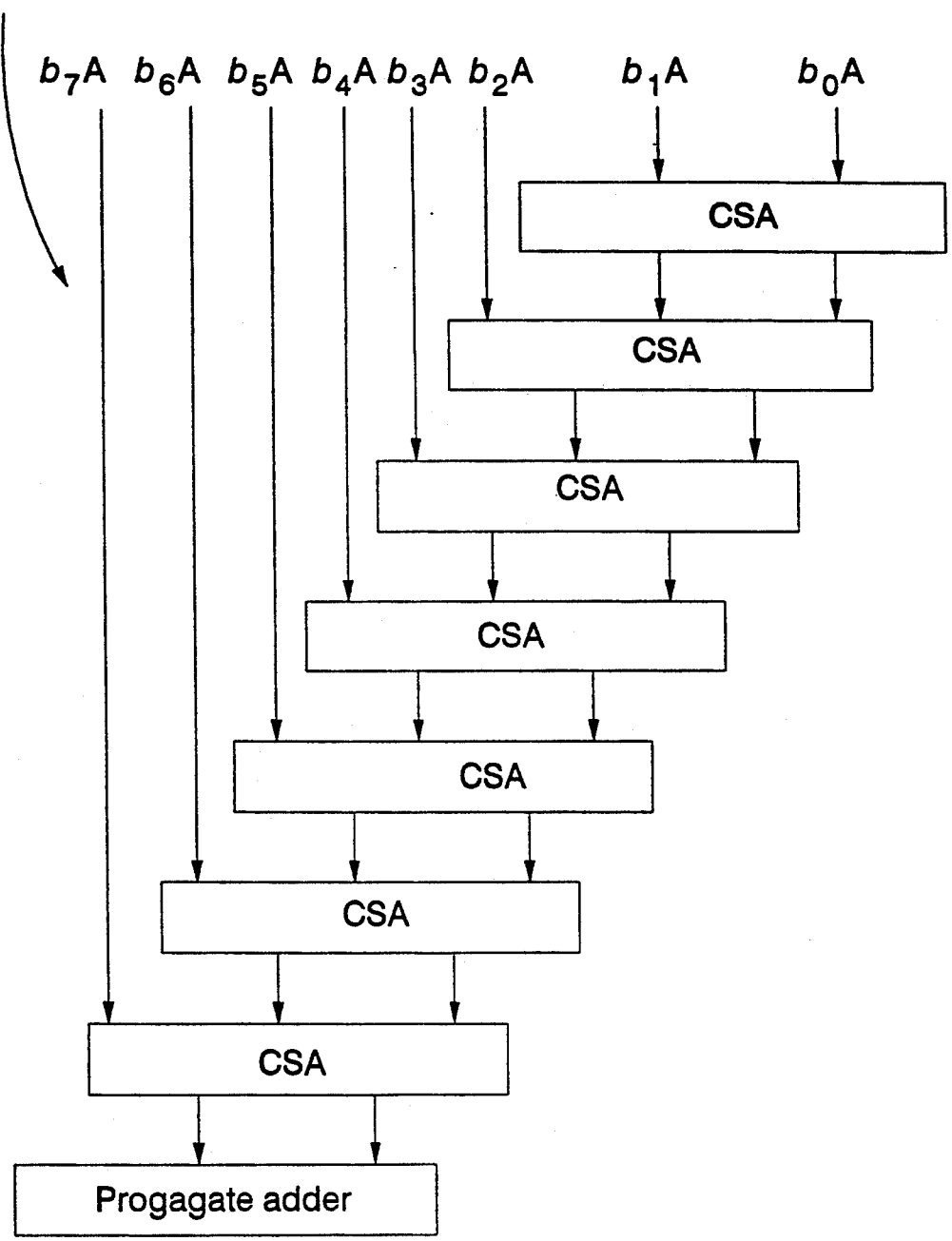
FIG. 2 illustrates a block diagram of an array multiplier.
Figure 3:
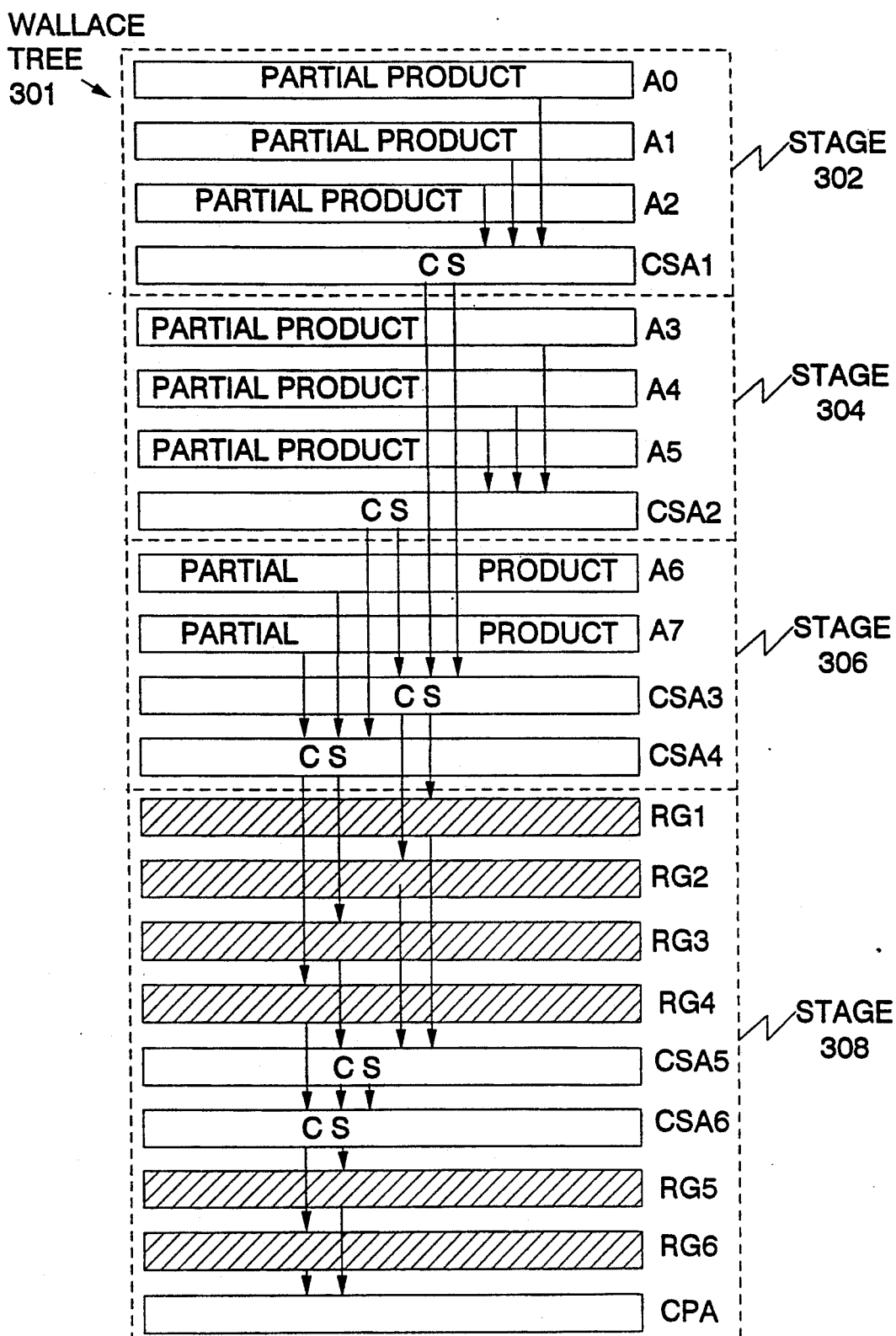
FIG. 3 illustrates a conventional Wallace Tree.
Figure 5:
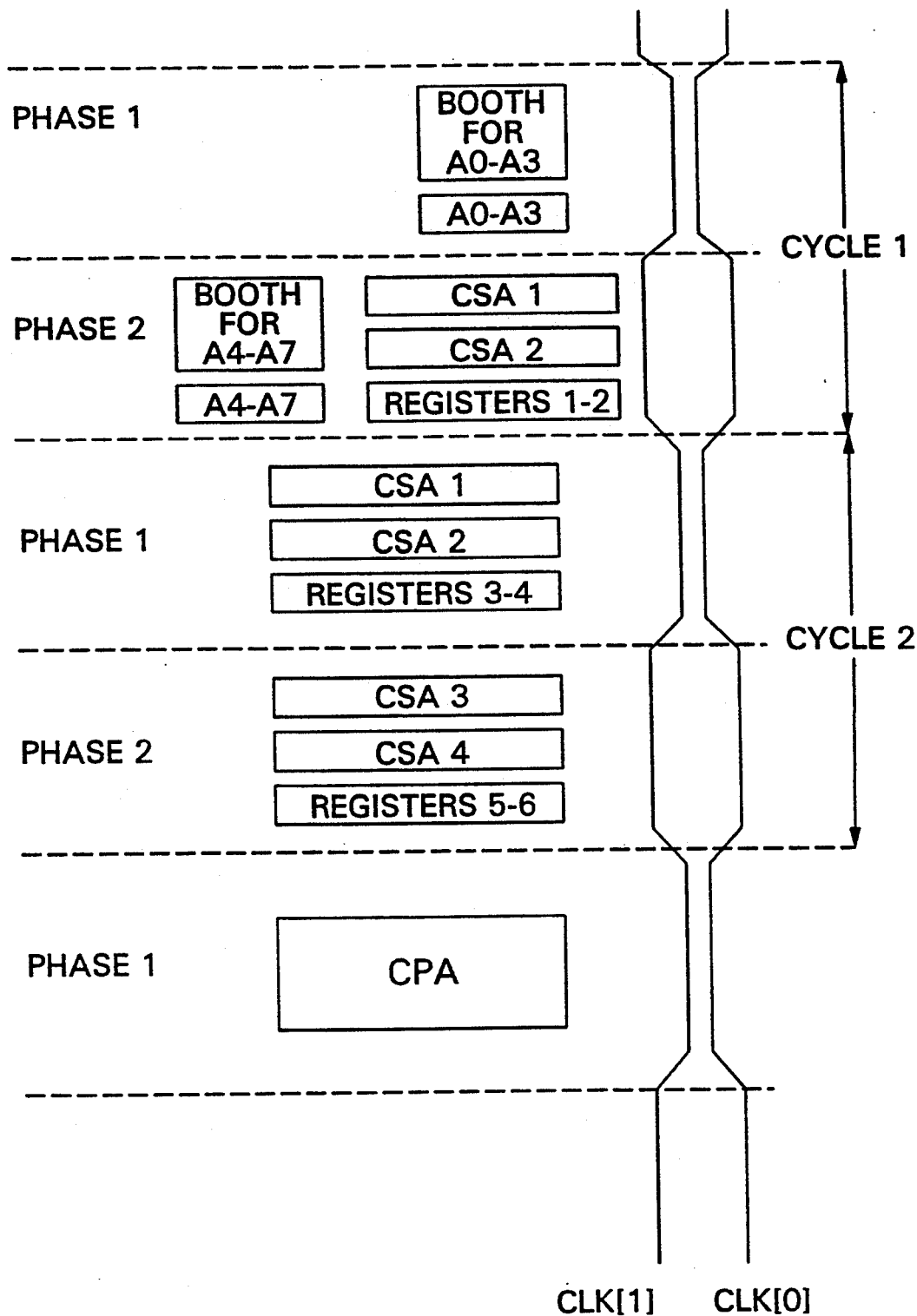
FIG. 5 illustrates a timing diagram according to the present invention.

FIG. 5 illustrates a timing diagram 500 according to the present invention. Timing diagram 500 includes data flow, machine cycles (1-3) and a two phase clock (CLK): CLK[0] and CLK[1]. The present invention has a latency time of approximately two and a half cycles, which is equivalent to or slightly longer than a conventional Wallace tree. However, as a result of this implementation there is regularity in structure and a significant reduction in chip area as compared to conventional Wallace Trees. Notice that less hardware is needed in FIG. 4 than FIG. 3 to obtain the same result. In particular, CSA 1 and CSA 2 are reused. In addition, unlike the set-up of FIG. 3 there is regularity with multiplier 402.

Referring to FIGS. 4 and 5, the following description illustrates how multiplier 402, performs multiplication. In a first phase of cycle 1, partial products A0-A3 are Booth coded and enter multiplier 402.

In a second phase of cycle 1, partial products A0, A1, and A2 are inputs to CSA 1. Carry 405 and sum 406, from CSA 1 are inputs to CSA 2. Since all CSAs require three inputs, partial product A3 is a third input to CSA 2. Results, or outputs, from CSA 2 are then latched into registers 1 and 2. Carry 409 is latched into register 2 and sum 410 is latched into register 1. Also in the second half of cycle 2, Booth coding for partial products A4-A7 are generated.

In a first phase of a cycle 2, partial products A4, A5, and A6 are inputs to CSA 1. Results from CSA 1, carry 405 and sum 406, are input to CSA 2. Partial product A7 functions as a third input of CSA 2. The results from CSA 2 are then latched into registers 3 and 4. In particular, carry 411 is latched into register 4 and sum 412 is latched into register 3.

In the second phase of cycle 2, the results latched in register 1, register 2 and register 3 are output to CSA 3 via data paths 413, 414 and 415, respectively. Outputs from CSA 3, sum 416 and carry 417 now function as two inputs for CSA 4. The results latched in register 4 is the third input 418 for CSA 4. Results from CSA 4 are then latched in registers 5 and 6. Sum 420 and carry 421 from CSA 4 are latched into registers 5 and 6, respectively.

In the first phase of cycle 3, data latched in register 5 is provided via data path 422 as an input for CPA 1. Likewise, data latched in register 6 via data path 423 is another input for CPA 1. Once data is fully loaded into CPA 1, the final product is determined by adding the final sum and carry from registers 5-6. Depending on the system, CPA 1 may be any number of bits wide. In the preferred embodiment CPA 1 is a 128 bit adder.

Registers 5 and 6, are needed for pipelining purposes, for storing results from CSA 4 before sending these results to CPA 1. Carry 421 and sum 420 from CSA 4 are typically determined faster than CPA 1 is able to generate the final product. Therefore, in order to account for CPA 1's slower speed, it is necessary to store the outputs from CSA 4 before passing them to a next stage to be added by CPA 1.

While various embodiments of the present invention have been described above, it should be understood that they have been presented by way of example only, and not limitation. Thus, the breadth and scope of the present invention should not be limited by any of the above-described exemplary embodiments, but should be defined only in accordance with the following claims and their equivalents.

What is claimed is:

1. A high-speed multiplier, comprising:
   a first carry-save adder (CSA);
   a second CSA coupled to said first CSA;
   first, second, third, and fourth registers coupled to said second CSA;
   a third CSA coupled to said first, said second and said third registers;
   a fourth CSA coupled to said fourth register and said third CSA;
   fifth and sixth registers coupled to said fourth CSA; and a carry-propagate adder coupled to said fifth and sixth registers.

2. A compact integrated circuit multiplier having Booth coded partial products as inputs, comprising:
   a first carry-save adder for receiving a plurality of partial product inputs and for generating a first sum and a first carry;
   a second carry-save adder, coupled to said first carry-save adder for receiving a further partial product input and said first sum and said first carry as inputs, and for generating a second sum and a second carry;
   registers means coupled to said second carry-save adder, for storing said second sum and said second carry;
   a third carry-save adder, coupled to said register means, for receiving said second sum and said second carry from said register means and for generating a third carry and a third sum;
   a fourth carry-save adder, coupled to said register means and said third carry-save adder, for receiving said second carry from said register means and for receiving said third carry and said third sum from said third carry-save adder, and for generating a fourth carry and a fourth sum; and
   a carry propagate adder, coupled to said fourth carry-save adder, for receiving said fourth carry and said fourth sum, and for adding said fourth carry with said fourth sum to obtain a final product.

3. The multiplier of claim 2, wherein said register means comprises a first register and a second register, said first register for storing said second sum, and said second register for storing said second carry.

4. The multiplier of claim 2, wherein said register means comprises a third register and a fourth register, said third register for storing said second sum and said fourth register for storing said second carry.

5. The multiplier of claim 2, further comprising a fifth register and a sixth register coupled between said fourth carry-save adder and said carry-propagate adder, said fifth register for storing said fourth sum from said fourth carry-save adder before passing said fourth sum to said carry-propagate adder, and said sixth register for storing said fourth carry from said fourth carry-save adder before passing said fourth carry to said carry propagate adder.

* * * * *